United States Patent [19]

Hashimoto et al.

[11] Patent Number: 5,773,277
[45] Date of Patent: Jun. 30, 1998

[54] **CRYSTALLINE CHONDROITINASE ISOLATED FROM *PROTEUS VULGARIS* ATCC 6896**

[75] Inventors: Nobukazu Hashimoto, Sayama; Hideo Mochizuki, Nagoya, both of Japan

[73] Assignee: Seikagaku Kogyo Kabushiki Kaisha, Tokyo, Japan

[21] Appl. No.: 445,206

[22] Filed: May 18, 1995

Related U.S. Application Data

[62] Division of Ser. No. 82,853, Jun. 23, 1993, Pat. No. 5,496,718.

[30] Foreign Application Priority Data

Jun. 26, 1992 [JP] Japan ................................. 4-192882
Oct. 26, 1992 [JP] Japan ................................. 4-310890

[51] Int. Cl.$^6$ ........................... C12N 9/88; C12N 9/44
[52] U.S. Cl. ........................ 435/232; 435/183; 435/188; 435/201
[58] Field of Search ................................. 435/232, 183, 435/188, 201

[56] References Cited

U.S. PATENT DOCUMENTS

| | | | |
|---|---|---|---|
| 3,549,500 | 12/1970 | Suzuki ................................... | 195/62 |
| 3,773,624 | 11/1973 | Wagner et al. ........................ | 435/229 |
| 4,696,816 | 9/1987 | Brown ..................................... | 424/94 |
| 5,198,355 | 3/1993 | Kikuchi et al. ........................ | 435/232 |

FOREIGN PATENT DOCUMENTS 3080079  8/1989  Japan ............................. C12N 1/20

OTHER PUBLICATIONS

Japan Patent Application JP 54107587 (Abstract).
Japan Patent Application JP 54107586 (Abstract).
Japan Patent Application JP 73032351 (Abstract).
Japan Patent Application JP 72013704 (Abstract).
Japan Patent Application JP 4330280 (Abstract).
Japan Patent Application JP 62122588 (Abstract).

M. Breen et al., "Microanalysis of Glycosaminoglycans" *Anal. Biochem.* 113:416–422 (1981).

N. Sato et al., "Depolymerization of Chondroitin C Sulfate by Immobilized *Proteus Vulgaris* Cells" *Biotech. and Bioeng.* 28:1707–1712 (1986).

N. Sato et al., "Cultural Conditions for the Induction of Chondroitinase ABC in *Proteus Vulgaris* Cells" *J. Ferment. Technol.* 64(2):155–159 (1986).

N. Sato et al., "Subunit Structure of Chondroitinase ABC from *Proteus Vulgaris*" *Agric. Biol. Chem.* 50(4):1057–1059 (1986).

*Primary Examiner*—David M. Naff
*Assistant Examiner*—Blaine Lankford
*Attorney, Agent, or Firm*—Testa, Hurwitz & Thibeault, LLP

[57] ABSTRACT

A crystallizable, purified chondroitinase ABC having a molecular weight of about 100,000 dalton by the measurement of the SDS-polyacrylamide gel electrophoresis (SDS-PAGE) and the measurement by the gel permeation chromatography method, having alanine as the N-terminal amino acid and proline as the C-terminal amino acid is disclosed. A process for the purification of the crystallizable purified chondroitinase ABC comprising removing nucleic acid from an surfactant solution extract obtained from cells of chondroitinase ABC-producing microorganisms and chromatographically treating by concentration gradient elution using a weak cation exchange resin or a strong cation exchange resin is disclosed. A composition comprising a chondroitinase and serum albumin, gelatin, or a nonionic surfactant is disclosed. The enzyme is isolated from *Proteus vulgaris* ATCC 6896.

5 Claims, 12 Drawing Sheets

5,773,277

CRYSTALLINE CHONDROITINASE ISOLATED FROM *PROTEUS VULGARIS* ATCC 6896

This is a divisional of application Ser. No. 08/082,853, filed Jun. 23, 1996, now U.S. Pat. No. 5,496,718.

BACKGROUND OF THE INVENTION

1. Field of the Invention

The present invention relates to a purified chondroitinase ABC and a crystallized chondroitinase ABC having an extremely high purity and excellent stability, a process for the preparation of the chondroitinase ABC and the chondroitinase ABC crystal, and a pharmaceutical composition comprising chondroitinase as an effective component.

2. Description of the Background Art

Chondroitinase ABC [EC 4.2.2.4] is an enzyme degrading hyaluronic acid, chondroitin sulfate, chondroitin, dermatan sulfate, or the like into a mixture of an unsaturated disaccharide and oligosaccharide. The enzyme is known to be produced by bacteria such as *Proteus vulgaris*.

For the preparation of chondroitinase ABC, a process which comprises subjecting a disrupted bacterial cell suspension progressively to a streptomycin treatment, an ammonium sulfate fractionation, a DEAE cellulose chromatography, and a phosphocellulose chromatography (J. Biol. Chem., 243, (7), 1523–1535 (1968)), and a process which comprises subjecting a disrupted bacterial cell suspension progressively to DEAE cellulose chromatography, hydroxyapatite chromatography, zinc-immobilized agarose chromatography, and gel permeation chromatography (Agric. Biol. Chem., 50, (4), 1057–1059 (1986); Japanese Patent Laid-open (kokai) No. 122588/1987), and the like are known.

On the other hand, the intervertebral disc dissolution method (Intradiscal therapy: chemonucleolysis) was developed for curing disc herniation which is identified as a cause of human lumbar pain. In this method, chymopapain which is a protease derived from papaya or a collagenase derived from bacteria is injected into the intervertebral disc antrum to remove the swelling capacity of the disc. Chymopapain is thus commercially sold in Europe and the United States as a drug under the trademark of Chymodiactin (Smith Laboratories) or Discase (Travenol).

However, the intradiscal therapy using said protease degrades not only the herniated disc, but also proteins in the surrounding tissues. This can be a cause of side effects such as neuroparalysis, allergy, and the like.

Mark R. Brown studied enzymes which can act on herniated disc with specificity and directed his attention to the degradation of proteoglycan which is a major herniated disc constituent. His study resulted in the intradiscal therapy using chondroitinase ABC or chondroitinase AC (U.S. Pat. No. 4,696,816).

In particular, the chondroitinase ABC produced by *Proteus vulgaris* is considered to be appropriate to medical and commercial applications because of its capability of selectively removing side chain of chondroitin sulfate or dermatan sulfate from proteoglycan, its inactivity toward keratan sulfate, heparin, and heparan sulfate, and its abundant productivity. Because of this, enzyme preparations having the chondroitinase ABC activity are prepared from culture products of *Proteus vulgaris* by aforementioned processes. These enzyme preparations, however, are not suitable for use as a drug for curing disc herniation or as a high-purity reagent, because they have protease activity or endotoxin activity and contain nucleic acid. They are unstable as enzyme proteins (J. Biol. Chem., 243, (7), 1523–1535 (1968); GB Patent 1067253, Agric. Biol. Chem., 50, (4), 1057–1059 (1986); Japanese Patent Laid-open (kokai) Nos. 122588/1987 and 57180/1990).

Especially, the presence of impurities and instability may cause serious problems when the chondroitinase ABC is used as a drug.

SUMMARY OF THE INVENTION

The subject of the present invention is therefore to provide a novel, high-purity chondroitinase ABC and crystallized chondroitinase ABC not containing impurities, having a high specific activity and excellent stability, and useful as a drug, and a process for preparing the chondroitinase ABC and crystallized chondroitinase ABC at a high yield.

Another subject of the present invention is to provide a pharmaceutical composition comprising chondroitinase as an effective component.

In order to resolve these subject, the present inventors have undertaken studies on the purification of chondroitinase ABC and found that a process comprising extracting the enzyme from cells of a microorganism, removing nucleic acid from the enzyme-containing extract, and treating the extract by chromatography in which a weak cation exchange resin and a strong cation exchange resin are combined produces a purified chondroitinase ABC from which impurities such as endotoxin, nucleic acid, protease, and the like have been completely removed and which shows a single band in SDS-PAGE and a single peak in HPLC (GPC: gel permeation chromatography, cation exchange).

The chondroitinase ABC thus obtained was found to be crystallized into a chondroitinase ABC crystal which has a specific activity three times higher than that of chondroitinase ABC preparations obtained by a conventional method, maintains its activity during a long-term storage, and is highly useful as a drug. These findings have led to the completion of the present invention.

Accordingly, an object of the present invention is to provide a chondroitinase ABC with a high purity and high stability, of which the characteristics are discussed hereinafter.

Another object of the present invention is to provide a process for preparing the chondroitinase ABC with a high purity and high stability which comprises, (i) a step of obtaining an enzyme-containing extract from cells of microorganism producing chondroitinase ABC (step 1), (ii) a step of removing nucleic acid from the enzyme-containing extract (step 2), and (iii) a step of chromatographic treatment, which comprises, (a) absorbing the chondroitinase ABC by a chromatographic treatment of said enzyme-containing extract using a weak cation exchange resin, eluting the absorbed enzyme, absorbing the enzyme in the eluate, and eluting the absorbed enzyme by chromatography using a strong cation exchange resin (step 3–1), or (b) absorbing the chondroitinase ABC by a chromatographic treatment of said enzyme-containing extract using a strong cation exchange resin, eluting the absorbed enzyme, absorbing the enzyme in the eluate, and eluting the absorbed enzyme by chromatography using a weak cation exchange resin (step 3-2).

In a preferred embodiment of the present invention, said extract of chondroitinase ABC is obtained by a method comprising adding a buffer solution with a pH in the neighborhood of neutral to wet cells to produce a cell suspension and subjecting the suspension to a physical treatment to pulverize the cells; or by a method comprising adding a surfactant solution with a pH in the neighborhood of neutral to wet cells to produce a cell suspension and stirring the suspension.

Said two-step chromatography by the combination of weak and strong cation exchange resins after removal of nucleic acid from the cell extract containing chondroitinase ABC produces a high-purity chondroitinase ABC which is purer and more stable than conventional chondroitinase ABC preparations and having a specific activity more than three times higher than that of chondroitinase ABC preparations obtained by a conventional method.

A still another object of the present invention is to provide a crystallized chondroitinase ABC having a needle-like or prismatic shape and the characteristics of said purified chondroitinase ABC, which is prepared by crystallizing said purified chondroitinase ABC in a polyether having hydroxyl groups at both ends (e.g., polyethylene glycol, polypropylene glycol).

Such a chondroitinase ABC and crystals thereof are highly homogeneous, has a stable quality and high specific activity, and exhibits excellent storage stability (e.g., its activity hardly decreases when allowed to stand for one month at about 25° to 40° C.).

A further object of the present invention is to provide compositions containing a chondroitinase.

Specifically, the present invention provides a composition comprising a chondroitinase and serum albumin or gelatin.

The present invention further provides a composition comprising a chondroitinase and a nonionic surfactant.

A still further object of the present invention is to provide a pharmaceutical composition for curing intervertebral disc displacement comprising a chondroitinase.

Not only the above-mentioned purified chondroitinase ABC, but also conventionally known chondroitinase ABC or chondroitinase AC can be used for these compositions.

Such compositions provide a solution which prevents absorption of chondroitinase to the wall of containers, and further prevents insoluble matters from being produced by mechanical stress, thus maintaining a high activity and useful as a drug.

Other and further objects, features and advantages of the present invention will appear more fully from the following description.

DETAILED DESCRIPTION OF THE INVENTION AND PREFERRED EMBODIMENTS

Figure 1:
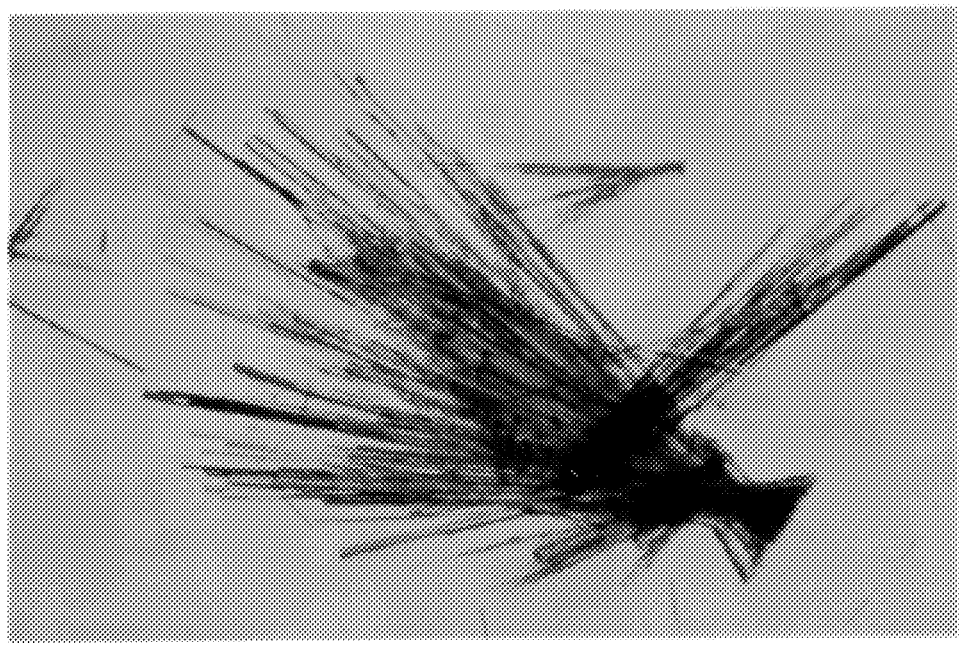
FIG. 1 is a microscopic photograph of the chondroitinase ABC crystal of the present invention.

Processes for preparing the purified chondroitinase ABC and the chondroitinase ABC crystal of the present invention are illustrated in detail.

Any cells of microorganisms conventionally known to produce chondroitinase ABC, for example microorganisms belonging to *Proteus vulgaris* or the like, can be used for the production of the chondroitinase ABC of the present invention. A specific example of such a microorganism is *Proteus vulgaris* NCTC 4636 (ATCC 6896, IFO 3988).

The microorganisms can be cultured by a conventional method (e.g., J. Biol. Chem., 243, (7), 1523–1535 (1968); Japanese Patent Laid-open (kokai) Nos. 122588/1987 or 57180/1990). Wet cells are collected from the culture and suspended into a buffer solution with a pH in the neighborhood of neutral to extract enzyme from the suspension. A phosphate buffer solution, Tris-HCl buffer solution, acetate buffer solution, or the like with a pH of 6.0 to 8.0 and a concentration of 1 to 100 mM is normally used as the buffer solution with a pH in the neighborhood of neutral. Cells are pulverized by a bead mill procedure (using DYNO®MILL or others) to extract an enzyme solution containing chondroitinase ABC, protease, other enzymes, nucleic acid, proteins, and the like.

The efficiency of the extraction of chondroitinase ABC from cells can be promoted even more by using a surfactant solution, used as a buffer solution to which a surfactant is added.

Any surfactants which can promote the enzyme-containing extraction efficiency can be used in the present invention. Nonionic surfactants are preferred as the surfactants.

Nonionic surfactants which can be used include polyoxyethylene alkyl ethers, polyoxyethylene p-t-octylphenyl ethers, polysorbate, and the like. Emulgen-type surfactants, Liponox-type surfactants, Brij-type surfactants, and the like are given as specific examples of polyoxyethylene alkyl ethers. Commercially available surfactants among these are Emulgen 120, Emulgen 109P, Liponox DCH, Brij 35, 78, 76, 96, 56, 58, 98, Nikkol BL-9EX, BL-21, BL-25, and the like. Given as specific examples of polyoxyethylene p-t-octylphenyl ethers are Triton-type surfactants, Nonidet P40-type surfactants, Igepal/CA-type surfactants, Polytergent G, Neutronyx-type surfactants, Conco-type surfactants, and the like. Among these types of surfactants, Triton X-100, X-45, X-114, X-102, X-165, X-305, X-405, Nonidet P-40, Igepal CA-630, Neutronyx 605, Conco NIX-100, and the like are commercially available. Tween-type surfactants, Emasol-type surfactants, Sorbester-type surfactants, Crill-type surfactants, and the like are given as specific examples of polysorbates. Sorbitan mono-9-octadecanoate poly(oxy-1, 2-ethanediyl) derivatives, commercially available as Tween 80, are preferred as polysorbate. Other examples of commercially available polysorbates are Tween 20, 40, 60, Emasol 4115, 4130, and the like.

Of the above surfactants, especially preferred are polyoxyethylene alkyl ether (e.g., polyoxyethylene lauryl ether, polidocanal; hereinafter referred to as "POELE"), and the like. The use of these surfactants not only promotes the enzyme-containing extraction efficiency, but also produces an enzyme-containing extract containing a chondroitinase ABC with less content of protease, concomitant protein and nucleic acid than other extraction method.

The enzyme-containing extract thus obtained is subjected to chromatography using a weak cation exchange resin or a strong cation exchange resin, and then a chondroitinase ABC with an extremely high activity, which exhibits a single band in electrophoresis, can be produced. No protease activity is detected in such chondroitinase ABC. Its endotoxin content is so small that there is no problem in using it as a drug component.

For the extraction, the cultured wet cells are added to a buffer solution containing 2 to 7% of said surfactants to produce a cell suspension. The cell suspension is warmed to the temperature range of 15 to 45° C., preferably about 370° C., stirred for about 1 to 10 hours, preferably about 2 to 6 hours, and cooled to room temperature, to separate an extract from a cell residue by a separation means such as centrifuge or the like. The extract thus obtained, which contains chondroitinase ABC, as a major component, other enzymes, proteins and nucleic acid, is transferred to the purification step.

In the purification step, proteins, nucleic acid, and the like are removed from the cell extract solution. Any conventional methods are applicable to the removal of proteins and nucleic acid. When the use of the enzyme as a drug component is taken into account, an especially preferred method to remove nucleic acid is adding protamine sulfate.

The treatment using protamine is carried out by adding 3 to 7% protamine sulfate aqueous solution to the cell extract to a final concentration of about 0.25 to 1% and stirring the mixture at about from 40° C. to room temperature for 10 to 30 minutes to produce precipitate of nucleic acid and the like. The precipitate is then separated and removed by centrifuge or the like.

The supernatant thus obtained, which contains chondroitinase ABC, protease, and other enzymes, is then chromatographically prepared by using a cation exchange resin.

In the preparation of the purified chondroitinase ABC, the purification is performed by the chromatography treatment using a combination of a weak cation exchange resin and a strong cation exchange resin.

A cation exchange resin having a carboxyalkyl group, e.g., carboxymethyl group, as an exchange group is exemplified as the weak cation exchange resin used here. A polysaccharide derivative (an agarose derivative, a crosslinked dextran derivative, etc.) having a carboxymethyl group as an exchange group is given as a specific example. Commercially available examples of such cation exchange resins are CM-Sepharose, CM-Sephadex, (trademarks, products of Pharmacia), and the like.

A cation exchange resin having a sulfoalkyl group as an exchange group is exemplified as the strong cation exchange resin used here. A polysaccharide derivative (an agarose derivative, a crosslinked dextran derivative, etc.) having a sulfoethyl group, a sulfopropyl group, or the like as an exchange group is given as a specific example. Commercially available examples of such strong cation exchange resins are S-Sepharose, SP-Sepharose™ (trademark, products of Pharmacia), SP-Sephadex™ (trademark, a product of Pharmacia), SP Toyopearl™ (trademark, a Tosoh Co.), and the like.

One example of the chromatography using these two types of cation exchange resins in combination is as follows.

The first chromatography is carried out by equilibrating the weak cation exchange resin with the same buffer solution (pH 6.5 to 7.5) used in the extraction of cells (e.g., 1 to 50 mM phosphate buffer solution, Tris-HCl buffer solution, acetate buffer solution, etc.), contacting said supernatant containing the enzyme with the cation exchange resin to absorb the enzyme, and washing the cation exchange resin, optionally using a salt solution (e.g., 20 to 25 mM NaCl solution) and/or the above-mentioned surfactant solution (e.g., 0.5% POELE solution). An eluant prepared by dissolving sodium chloride into said buffer solution at a concentration of about 0.1M is contacted with said resin to elute fractions having an activity of the enzyme. Either gradient elution or stepwise elution can be used as a method of the elution. The chromatography treatment can be carried out either by a column method or a batch method.

The fractions thus obtained is then contacted with a strong cation exchange resin which has been equilibrated with the same buffer solution to absorb chondroitinase ABC. After washing the cation exchange resin, optionally using a salt solution (e.g., 20 to 50 mM NaCl solution) and/or water, the chondroitinase ABC is isolated by gradient elution using the same type of buffer solution (e.g., phosphate buffer solution, Tris-HCl buffer solution, acetate buffer solution, etc.), but containing NaCl with a concentration gradient of 0 to 0.5M, preferably about 25 to 350 mM. This chromatography treatment is preferably carried out by the column method.

It is possible to reversibly perform the above chromatography using the two types of cation exchange resins.

When cells are extracted with a buffer solution containing a surfactant, the extract contains only very small amount of impurities. The enzyme, in this case, can be purified by a simple procedure, e.g., without the treatment of removing nucleic acid from the extract such as protamine treatment, only by passing the extract through a weak cation exchange resin (e.g, CM-Sepharose™) column to absorb chondroitinase ABC, washing the column, and eluting the enzyme with a gradient method.

The purified enzyme solution obtained by the chromatography may be served as a drug, a reagent, or the like, as is, after concentration and desalting. Alternatively, the concentrated and desalted enzyme solution may be made into powder by a common drying method (e.g., lyophilization) under conditions which do not inactivate or denature the enzyme.

In addition, the above purified enzyme solution may be blended and contacted with polyether having hydroxy groups at both ends (e.g., polyethylene glycol, polypropylene glycol, etc.) to crystallize the chondroitinase ABC. The crystals are rhombic or monoclinic system needle-like crystals, exhibiting crystal parameters shown in Examples hereinafter.

One example of the crystallizing procedure is as follows. Polyethylene glycol with an appropriate molecular weight, such as MW of 4,000, 6,000, or he like, is added to the enzyme solution. The solution, being adjusted to the concentration of the enzyme 250 to 500 U/ml and the concentration of polyethylene glycol 5 to 20%, preferably 10 to 15%, is allowed to stand at a temperature from 4° C. to room temperature until the crystal of the enzyme grows up.

Purified chondroitinase ABC thus obtained does not contain impurities such as endotoxin, nucleic acid, protease, other proteins, and the like, shows a single band in SDS-PAGE and a single peak in HPLC (GPC, cationic exchange), and has a specific activity three times higher than that of chondroitinase ABC obtained by a conventional method. In addition, according to the process of the present invention, in which procedures such as the ammonium sulfate fractionation, the concentration/desalting, and the like are not required in the course of the production as in the conventional processes, the time for the manufacture of the chondroitinase ABC can be shortened, the yield is promoted, and the manufacturing cost can be reduced. Furthermore, the process of the present invention can be applied with these advantages regardless of the amount of the chondroitinase ABC to be prepared.

Chondroitinase ABC crystal produced by the crystallization method mentioned above is needle-like or prismatic in shape (see FIG. 1), homogeneous, and stable in its quality. It has also a high specific activity and excellent storage stability The characteristics of the chondroitinase ABC obtained by the process of the present invention illustrated above are as follows.

(1) Actions

Act on hyaluronic acid, chondroitin sulfate, chondroitin, and dermatan sulfate, producing a small amount of a large molecular weight unsaturated oligosaccharide in an early stage of the reaction and, ultimately, a mixture of unsaturated disaccharide ($\Delta^4$-glucuronyl-N-acetylhexosamine and its 4- or 6-sulfate) and oligosaccharide.

(2) Optimum pH and Stable pH

Figure 2:
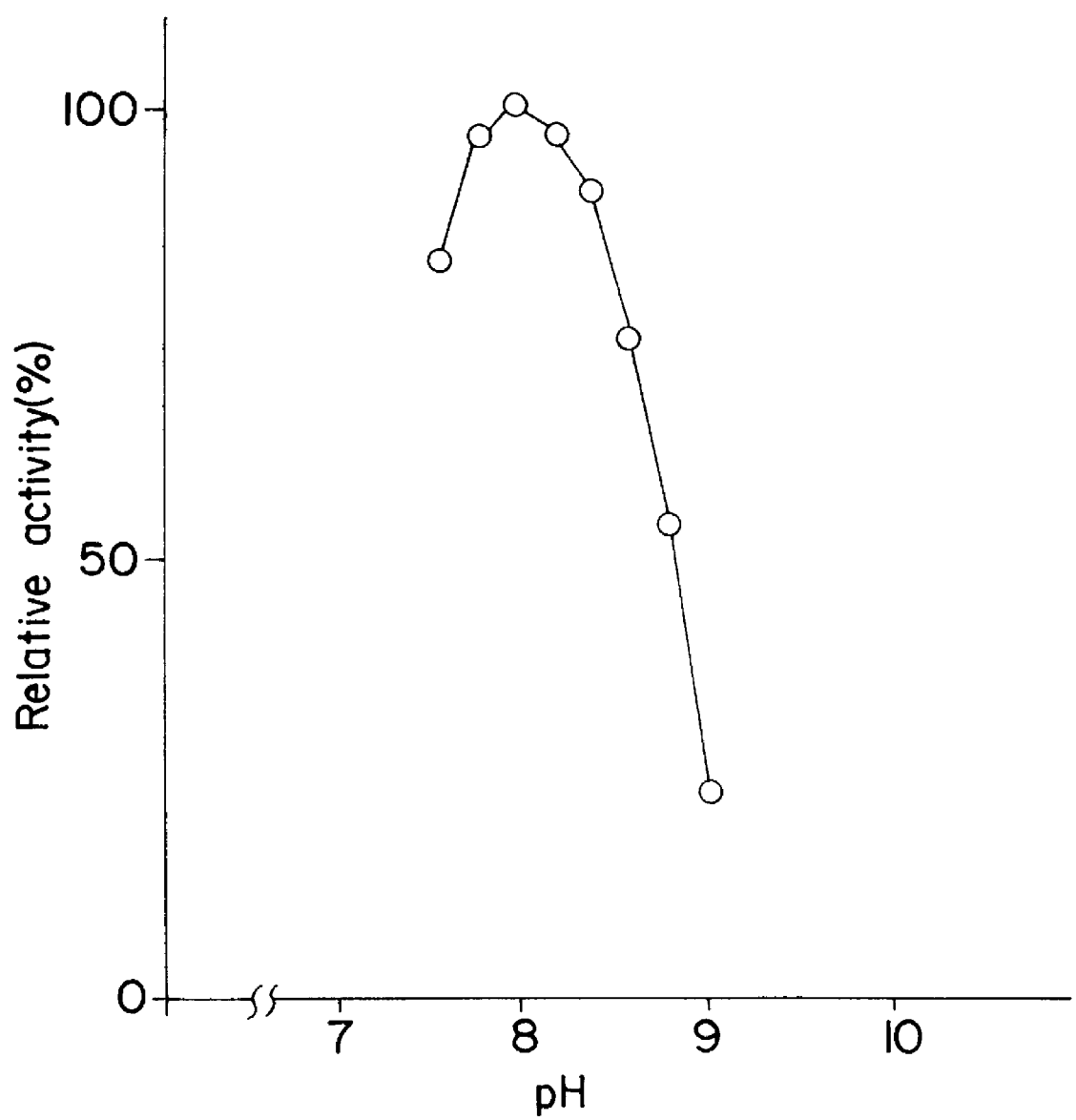
FIG. 2 shows a relationship between the activity and the reactive pH of the chondroitinase ABC of the present invention.
Figure 3:
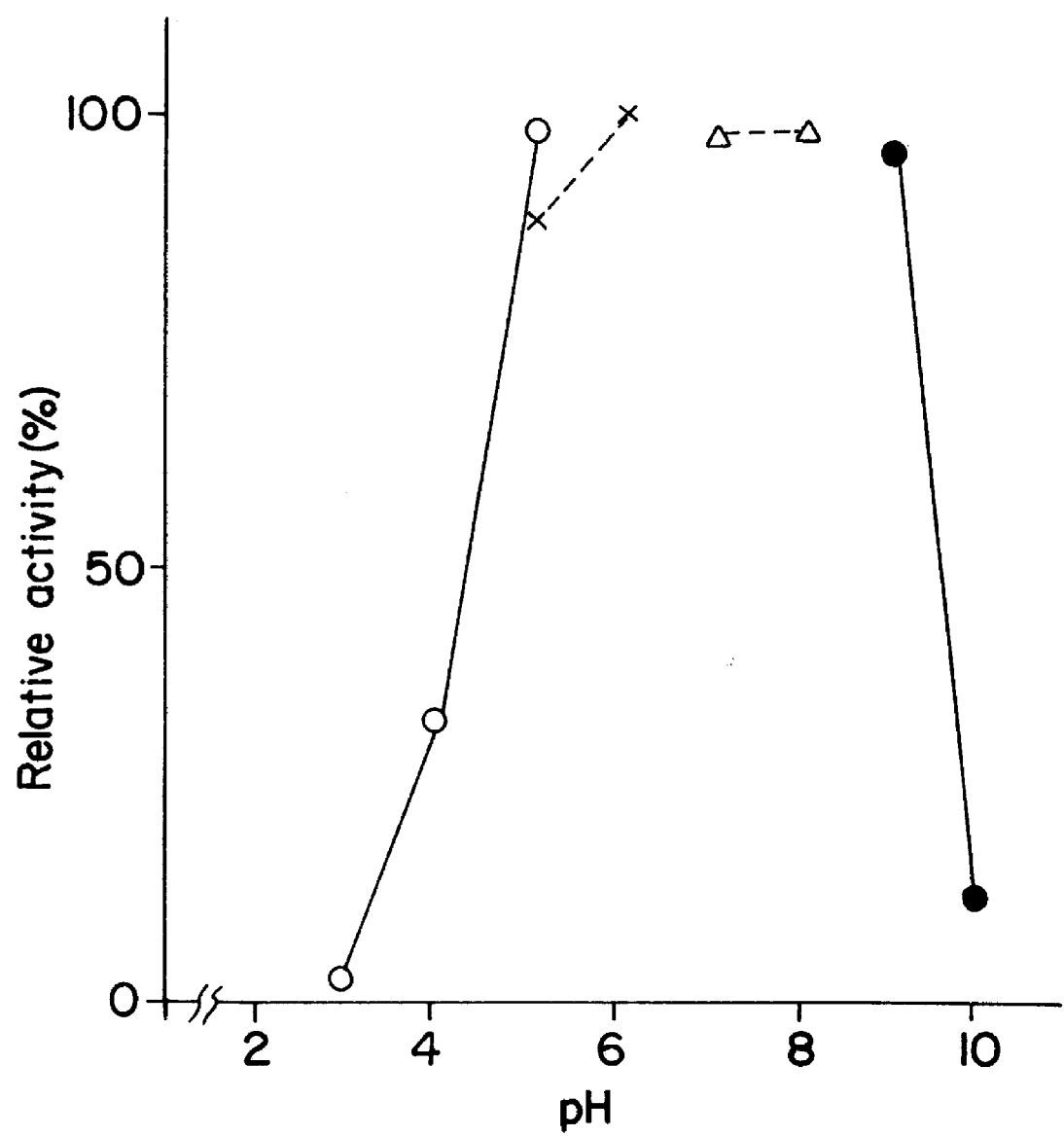
FIG. 3 shows relationships between pH and the residual activity of chondroitinase ABC of the present invention, when the enzyme was allowed to stand at 25° C. for 24 hours in various buffer solutions at a certain pH, wherein the line connected by open circles shows the residual activity when the enzyme was kept in a acetate buffer solution; the dotted Dine connected by crosses, a Tris-acetic acid buffer solution; dotted line connected by triangles, a Tris-HCl buffer solution; and the line connected by solid circles, a glycine buffer solution.

Optimum pH is 8.0 to 8.2, when chondroitin sulfate C is a substrate in a Tris-HCl buffer solution (FIG. 2). When allowed to stand at pH 5 to 9 at 25° C. for 24 hours, the enzyme exhibits about 80% or more of residual activity (FIG. 3).

(3) Assay of Enzyme Activity

The measurement is based on the production of unsaturated disaccharides exhibiting a remarkable absorbance of the light in the ultraviolet region by an enzymatic reaction. Specifically, the enzyme reaction is carried out in an enzyme reaction solution containing the enzyme, 1.2 mg of chondroitin sulfate C (substrate), 50 mM Tris-HCl buffer solution (pH 8 to 8.5) containing 50 mM sodium acetate, and 10 µg of casein at 37° C. for 20 minutes. The reaction is terminated with the addition of 0.05M HCl (pH 1.8). The absorbance at 232 nm is then measured. Separately, a heat denatured enzyme solution, as a control, is kept in a substrate solution with the same composition as above and treated in the same manner as above to measure the absorbance at 232 nm. The amount of unsaturated disaccharides is calculated from the increase in the absorbance of the sample over the control. In the calculation, the millimole molecular extinction coefficient of 2-acetamido-2-deoxy-3-0-($\beta$-D-gluco-4-ene-pyranosyluronic acid)-6-0-sulfo-D-galactose was assumed to be 5.5. As a result, one unit (U) of the enzyme is defined to be an amount of the enzyme catalyzing a reaction releasing 1 micromol of unsaturated disaccharides in one minute under the above-mentioned reaction conditions.

(4) Optimum Temperature of Reaction and Temperature Stability

Figure 4:
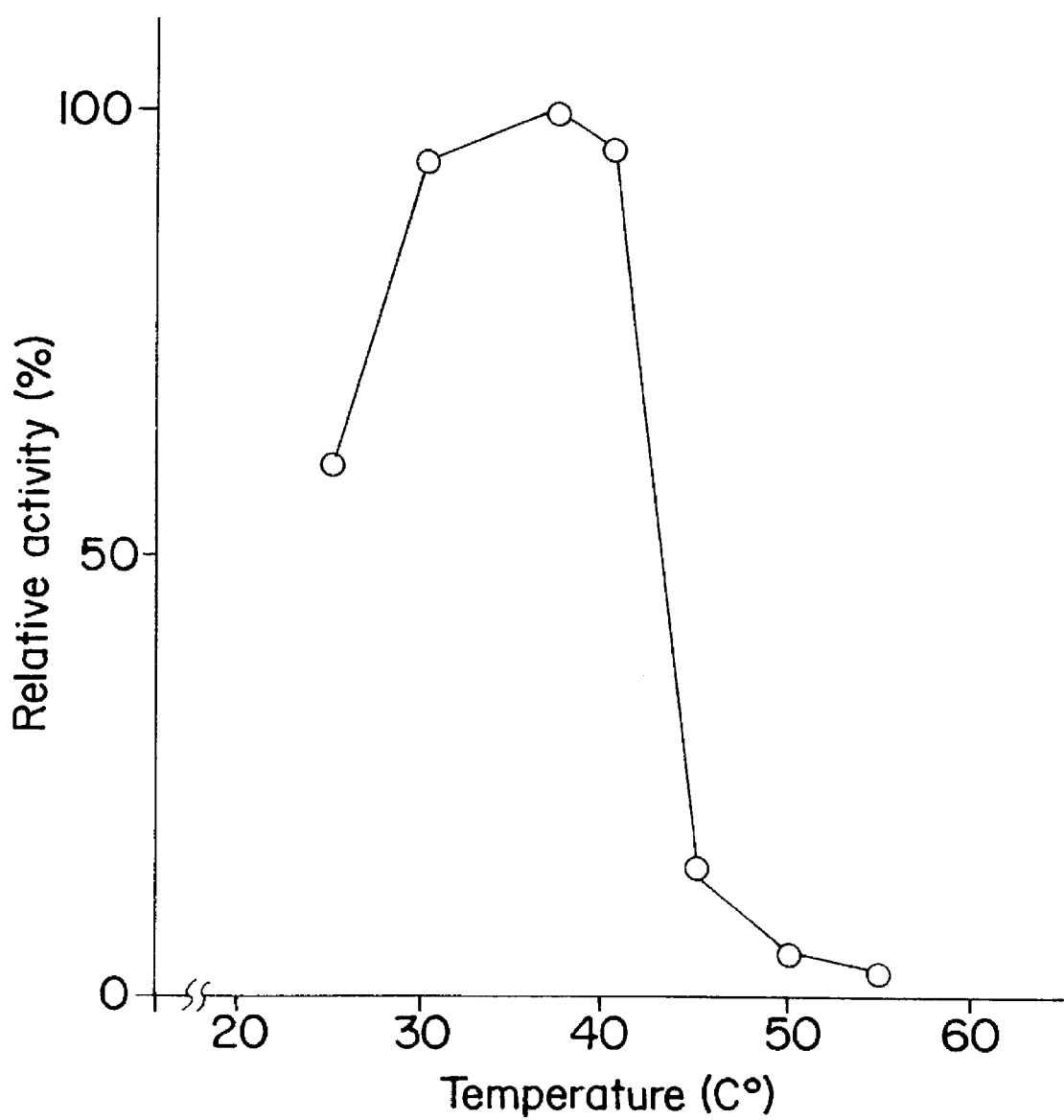
FIG. 4 shows a relationship between the residual and the reactive temperature of the chondroitinase ABC of the present invention.
Figure 5:
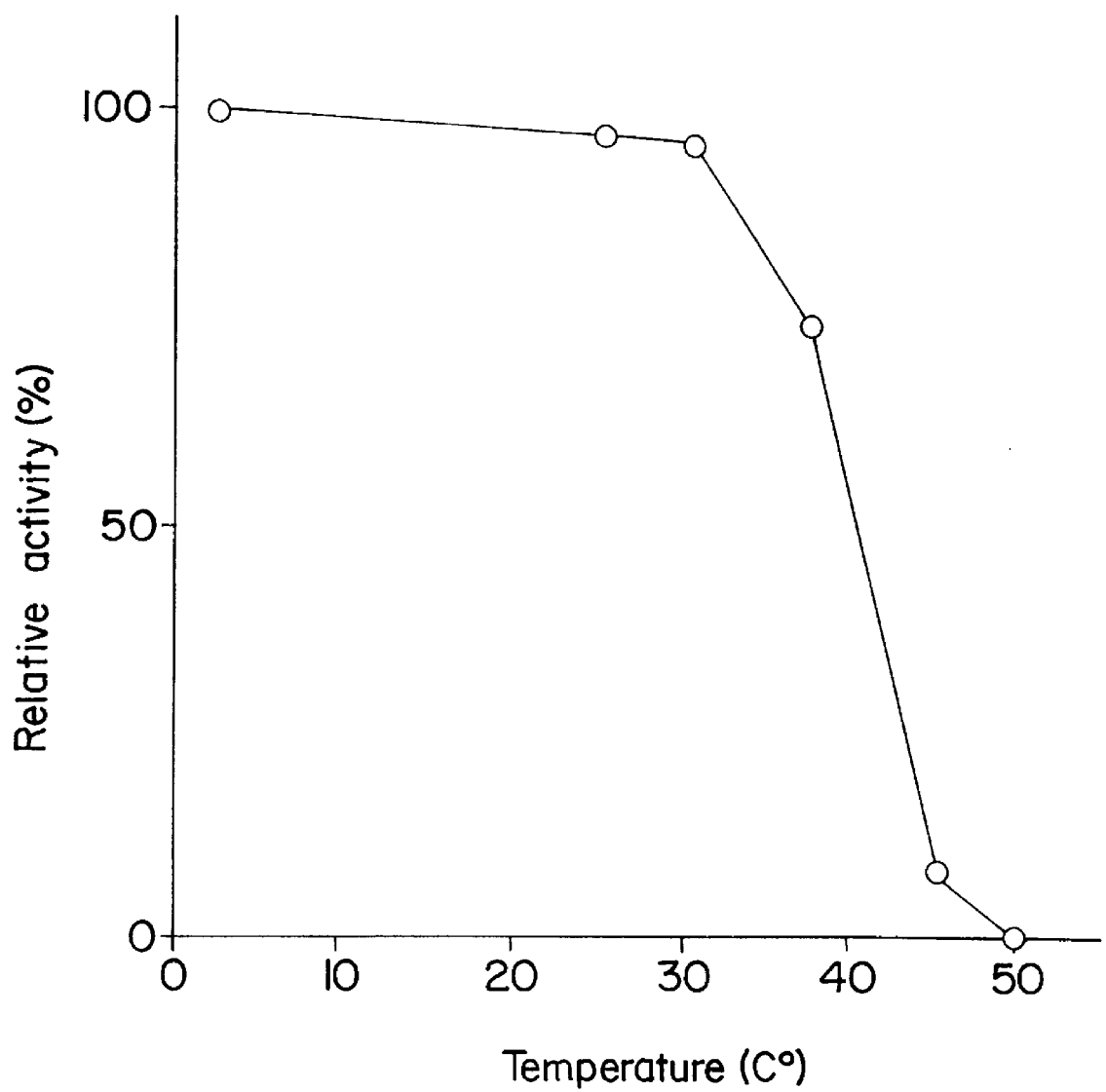
FIG. 5 shows a relationship between the residual activity of the chondroitinase ABC of the present invention and temperatures when the enzyme was kept in different temperatures for one hour.

The optimum temperature of reaction is 37° C., and the enzyme exhibits about 90% or more activity at 30 to 37° C. (FIG. 4). The enzyme was stable between 2° C. and 30° C. and inactivated at 50° C., when it was kept at different temperatures in a Tris-HCl buffer solution (pH 7.0) for 1 hour (FIG. 5).

(5) Inhibition

The activity is inhibited by zinc ion ($Zn^{2+}$), nickel ion ($Ni^{2+}$), iron ion ($Fe^{3+}$), and copper ion ($Cu^{2+}$) as shown in Table 1.

TABLE 1

| Compound | Concentration (mM) | Relative activity (%) |
|---|---|---|
| Not added | — | 100 |
| $ZnCl_2$ | 2 | 1.2 |
| $CuCl_2.2H_2O$ | 2 | 1.2 |
| $NiCl_2.6H_2O$ | 2 | 4.2 |
| $FeCl_3.6H_2O$ | 0.2 | 5 |

(6) Molecular Weight

Exhibits a single band by sodium dodecyl sulfate-polyacrylamide gel electrophoresis (SDS-PAGE). The molecular weight is about 100,000 dalton in both reduced and unreduced states. The molecular weight measured by the gel permeation chromatography (HPLC) was about 100,000 dalton (See FIG. 6; the conditions are discussed below).

(7) Isoelectric Point

Isoelectric point was about 8.2 and 8.5 (Phast Gel IEF pH 3 to 9 and a pI calibration kit 3-10, as a standard, were used in Phast System; all reagents and apparatus used were made by Pharmacia).
(8) Amino acid analysis
Shown in Table 2.

TABLE 2

| Amino acid | Number of residue per molecule |
|---|---|
| Asp | 106 |
| Thr | 51 |
| Ser | 63 |
| Glu | 87 |
| Gly | 53 |
| Ala | 50 |
| Val | 37 |
| Met | 16 |
| Ile | 45 |
| Leu | 76 |
| Tyr | 32 |
| Phe | 34 |
| Lys | 54 |
| His | 18 |
| Arg | 28 |
| Pro | 34 |

The above analysis was carried out by hydrolyzing chondroitinase ABC in 6M hydrochloric acid under reduced pressure at 110° C. for 24 hours. Three samples were analyzed and the average values were given in Table 2. The calculation was made taking the total molecular weight as 100,000. Trp and Cys were not measured.

(9) Terminal amino acid

The N-terminal amino acid residue identified by the Edman degradation analysis ("Biochemistry Experiments No. 1, Protein chemistry II, Determination of primary structure", 132–142, Aug. 28, 1976, published by Tokyo Kagaku Dojin) was alanine. The N-terminal amino acid sequence was Ala-Thr-X-Asn-Pro-Ala-Phe-Asp-Pro- (Sequence ID No. 1), wherein X means undetermined.

The C-terminal amino acid sequence identified by the carboxy peptidase method ("Biochemistry Experiments No. 1, Protein chemistry II, Determination of primary structure", 203–211) was -Ser-Leu-Pro (Sequence ID No. 2).

The terminal amino acid sequence of the chondroitinase ABC of the present invention is thus proven to be as follows.

Ala-Thr-X-Asn-Pro-Ala-Phe-Asp-Pro- - -Ser-Leu-Pro, wherein X is undetermined.
(10) Storage Stability The enzyme is stable for at least three months at room temperature either in a solution in phosphate buffer (pH 6 to 8) or under a dry condition.

(11) Specific Activity

Protein content was measured by Lowry method using bovine serum albumin as a standard. The specific activity is at least 300 U/mg of protein.

(12) Others

The enzyme exhibits a single peak in both cation exchange HPLC and gel permeation (GPC) HPLC.

The conditions and the results of the gel permeation chromatography were as follows.

Conditions

Column: TKS G3000SW$_{XL}$ (a product of Tosoh Co.)
Eluent: 0.1M phosphate buffer solution (pH 7.0) containing 0.2M NaCl
Elution rate: 0.5 ml/minute
Processing temperature: 35° C.
Detection wavelength: 280 nm Amount charged: 20 $\mu$l
Molecular weight marker:
Cytochrome C (12.4 kilo dalton)
Adenylate kinase (32 kilo dalton)
Enolase (67 kilo dalton)
Lactate dehydrogenase (142 kilo dalton)
Glutamate dehydrogenase (290 kilo dalton)
(Enzymes are all manufactured by Oriental Yeast Manufacturing Co. Ltd.)

Results

Figure 6:
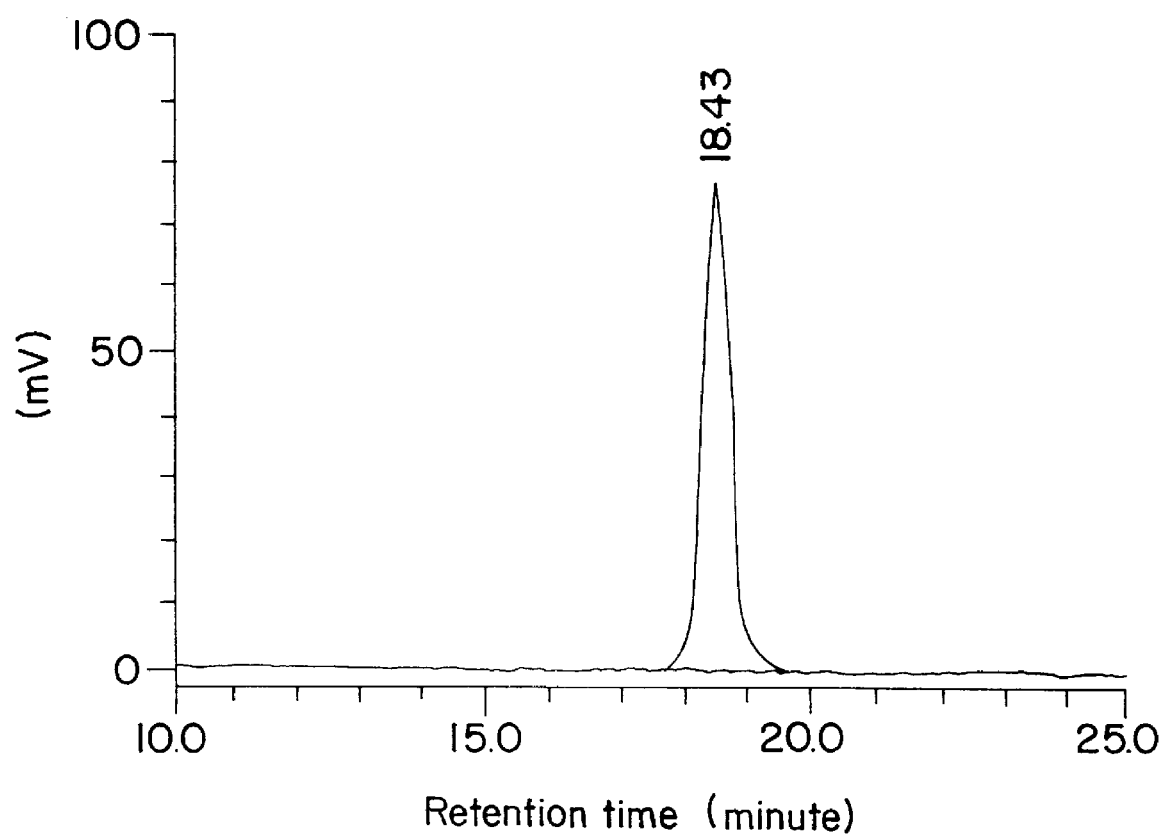
FIG. 6 shows a chromatogram when the chondroitinase ABC of the present invention was subjected to gel permeation by HPLC.

The chondroitinase ABC of the present invention was eluted as a single peak at a retention time of 18.43 minutes (FIG. 6). The molecular weight of the enzyme was determined to be about 1000,000 dalton based on the comparison of the retention time and the above molecular weight markers.

It did not substantially contain endotoxin. The DNA and protease contents were below the detection limit, while a commercial chondroitinase ABC (Seikagaku Corporation, Catalog No. 100332) contained DNA amounting 5,000 times of the detection limit and protease 200 times.

In the comparison of the chondroitinase ABC of the present invention and Chondroitinase ABC protease-free (Seikagaku Corporation, Catalog No. 100332) which is known to have the highest purity among currently known chondroitinase ABCs, the former has a molecular weight of about 1000,000 dalton in both the SDS-PAGE and HPLC (GPC), while the latter has a molecular weight of about 80,000 dalton in the SDS-PAGE and about 120,000 to 145,000 dalton in the gel filtration. This is a great difference between the two. In addition, while the former has a specific activity of 300 U/mg protein or more, the latter has a specific activity of about 110 U/mg protein. With respect to the storage stability, while the former is stable at room temperature for at least three months, the latter is claimed to be stable at −70° C. for at least three months. This is also a significant difference. Furthermore, the former chondroitinase ABC exhibits a single band in SDS-PAGE and a single peak in HPLC (GPC) and can be crystallized, and thus its terminal amino acid can be determined and its isoelectric point can be measured, whereas the latter is not an enzyme which can be identified as a substance, and, therefore, it is impossible to identify its terminal amino acid and to measure an isoelectric point.

The compositions and the drugs of the present invention is now discussed.

First, illustrating the composition and the drug comprising chondroitinase and serum albumin or gelatin, such a composition can be prepared by providing an aqueous solution containing additives mentioned below and having an adjusted pH; mixing this solution with purified chondroitinase having a specific activity of, for example, 300 U/mg or more, to produce an aqueous solution containing 5 U/mL or more, preferably 10 to 1,000 U/mL, of the purified chondroitinase; and optionally subjecting the solution to filtration to sterilize to make a liquid composition. This liquid composition may further be processed into a dry composition, preferably a lyophilized composition, by a drying treatment under unheated conditions such as lyophilization or the like. Alternatively, the liquid composition may be frozen at −20° C. to −80° C.

Essential additives mixed with purified chondroitinase in the composition of the present invention are proteins such as serum albumin or gelatin. These may be used together.

Serum albumin of mammals, e.g., human, cattle, horse, swine, sheep, goat, etc., are given as examples. Human serum albumin (HSA) which is applicable to parenteral administrations is preferred, when the composition is used as injection preparation for human. For example, human serum albumin prepared from plasma of healthy persons as a raw material and fractionated and purified by the Cohn's ethanol fractionation method can be used. Especially preferred is serum albumin treated with heat, preferably at about 60° C. for about 10 hours, to deactivate hepatitis virus and the like. HSA may contain sodium N-acetyltryptophan and/or sodium caprylate added thereto as stabilizers.

As example of gelatin, gelatin derived from animals such as cattle or swine can be given. Specifically, gelatin used here is prepared by appropriately treating collagen obtained from skin, bone, and the like of animals to solubilize, Such gelatins include acid treated gelatin (A-type) which has been treated with a mineral acid (pH 1 to 3, e.g., hydrochloric acid, sulfuric acid, sulfurous acid, phosphoric acid, etc.) and having an isoelectric point of 7.0 to 9.0, and alkali treated gelatin (B-type) which has been treated with an alkali (e.g, lime, etc.) and having an isoelectric point of 4.5 to 5.0. The acid treated gelatin is more preferred as gelatin used in the present invention. As examples of the acid treated gelatin, given are commercially available Nippi high grade gelatin (Type A) and the like.

The composition of the present invention is normally adjusted to pH 5 to 9, preferably pH 6 to 8, when it is a solution. For this purpose, it usually contains a buffer agent which can maintain the pH within these ranges. There are no specific limitations as to the types of buffer agents used in the present invention, so long as the same is physiologically acceptable. Examples of such buffer agents include those containing one or more compounds selected from the group consisting of hydrochloric acid, sodium hydroxide, sodium carbonate, sodium hydrogen carbonate, phosphoric acid, potassium dihydrogenphosphate, dipotassium hydrogenphosphate, sodium dihydrogenphosphate, disodium hydrogenphosphate, aminoacetic acid, sodium benzoate, citric acid, sodium citrate, acetic acid, sodium acetate, tartaric acid, sodium tartarate, lactic acid, sodium lactate, ethanolamine, arginine, and ethylenediamine. Especially preferred is a phosphate buffer. If pH is smaller than 5 or greater than 9, chondroitinase may be inactivated or insoluble matters may be produced in the solution.

Although an amount of 0.001 time or more by weight of such added proteins for the amount of the protein of chondroitinase exhibits a recognizable effect, a preferable amount is 0.01 to 500 times by weight, and particularly 0.05 to 100 times by weight. Even though an amount exceeding 500 times by weight may bring about the effect of the present invention, the enzyme activity per unit weight is reduced in such a large amount. The concentration of the buffer agent in the composition is 1 to 100 mM, and preferably 10 to 50 mM.

In addition to these additives, the composition of the present invention may contain additives conventionally added to pharmaceutical compositions, such as isotonizing agents, excipients, preservatives, soothing agents, and the like. For example, there are no restrictions as to excipients so long as they are commonly used for injection preparations, with preferred examples being creatinine, lactose, mannitol, purified sucrose, xylose, and the like.

The composition of the present invention is mainly used as injection preparations or a raw material of injection preparations containing chondroitinase as an effective component. Solution compositions are filled in containers such as ampules or vials, and distributed or stored, and served as injection preparations as are. It is possible to dry or freeze the solution composition in suitable containers for distribution and storing. Such a dry or frozen composition is dissolved with distilled water for injection, physiological saline, or the like, or liquefied before administration. These injection preparations can be used as an agent containing chondroitinase as an effective component for curing disc herniation. Such a curing agent can be used for the intervertebral disc dissolution method wherein herniated disc is dissolved by injecting it into intervertebral disc space of the patients. Although a dose cannot be generically specified and varies depending on the symptoms, age, and the like, normally an amount of about 10 to 300 U per dose is used in the case of chondroitinase ABC.

Illustrating now the composition and the drug of the present invention comprising chondroitinase and a nonionic surfactant, the additives to be mixed with chondroitinase in such a composition is a nonionic surfactant and a buffer agent. Preferred nonionic surfactants which can be added include polyoxyethylene sorbitan fatty acid esters (polysorbate), polyoxyethylene hydrogenated castor oil, sucrose fatty acid esters, polyoxyethylene polyoxypropylene glycol, and the like. As examples of polyoxyethylene sorbitan fatty acid esters, polyoxyethylene sorbitan (the polymerization degree=about 20) monolaurate, monopalmitate, monooleate, monostearate, trioleate, and the like are given. As commercial products, Polysorbate 80 (Tween 80) (polyoxyethylene (20) sorbitan monooleate), Polysorbate 60 (polyoxyethylene(20)sorbitan monostearate), Polysorbate 40, Tween 21, 81, 65, 85, and the like are named. As examples of polyoxyethylene hydrogenated castor oil, given are commercially available HCO-10, HCO-50, HCO-60, and the like. As sucrose fatty acid esters, commercially available DK ester F-160 and the like are exemplified. Pluronic F-68 and the like are given as examples of commercially available polyoxyethylene polyoxypropylene glycol.

As buffer agents, any physiologically acceptable buffer agents can be used. The aforementioned buffer agents can be used for this type of composition as well, with a phosphate buffer, e.g., a sodium phosphate buffer solution and a potassium phosphate buffer being particularly preferred. A liquid pharmaceutical composition of this type is adjusted to a pH region of 5 to 9, and preferably 6 to 8, by the addition of a buffer solution. When the pH is smaller than 5 or greater than 9, the chondroitinase may deactivated or insoluble matters may be formed in the solution.

Regarding the amount of these additives to be incorporated, although an amount of 0.06 time or more by weight of the nonionic surfactant for the-amount of chondroitinase exhibit the recognizable effect, a preferable amount is 0.6 to 300 times. The concentration of the buffer agent in the solution composition is 1 mM or more, and preferably 10 to 50 mM.

This type of composition may be processed into a final product form after the further addition of the aforementioned additives, such as isotonizing agents, excipients, preservatives, soothing agents, and the like. The preparation thus obtained can be used as a curing agent for intervertebral disc displacement in the same manner as described above, and can provide a solution which prevents adsorption of chondroitinase to the wall of containers and formation of insoluble matters from being produced by mechanical stress.

Summarizing the effects of the present invention, since the purified chondroitinase ABC of the present invention is remarkably high pure and contains no substantial amount of protease, nucleic acid and endotoxin, it is extremely useful as a drug and a reagent for use in research and experiments.

Because the purified chondroitinase ABC of the present invention has superior storage stability, its activity is hardly lost when it is used as a drug. Its high specific activity and minimal impurity content makes it possible to minimize a dose and prevents occurrence of side effects.

Regarding the effects of the purified chondroitinase ABC of the present invention as a reagent for experiments in research, it can promote the reproducibility of experimental results when it is used for experiments using animal cells, for example, since the enzyme contains no endotoxin and protease.

Furthermore, elimination of the conventionally required ammonium sulfate fractionation and omission of concentration/desalting procedure in the purification process according to the process of the present invention resulted in the reduction in the purification steps and the time for the processing, the promotion of the yield, and the decrease in the production costs.

Other features of the invention will become apparent in the following description of the exemplary embodiment which is given for illustration of the invention and is not intended to be limiting thereof.

EXAMPLE

Example 1

Proteus vulgaris (NCTC 4636, ATCC 6896, IFO 3988) was cultured by a commonly known method (J. Biol. Chem., 243, (7), 1523–1535 (1968)) to obtain cultured wet cells. To 200 g of the cells was added 600 mL of 5 mM phosphate buffer solution (pH 6.5 to 7.0) to make a suspension. The cells were pulverized using the Dyno® Mill and centrifuged to obtain an enzyme-containing extract solution (step 1).

Protamine sulfate was used to remove nucleic acid from the cell extract solution. A 5% protamine sulfate aqueous solution was added to said enzyme-containing extract solution to a final concentration of 0.5%. The mixture was stirred at 4° C. for 30 minutes and the produced precipitate was removed by centrifuge, thus obtaining a supernatant (step 2).

After the addition of about 5 times by volume of water, the supernatant was purified by column chromatography. Specifically, a column packed with CM-Sepharose™ was equilibrated with 5 mM phosphate buffer solution (pH 6.5 to 7.0), following which the supernatant was charged into the column for absorbing the enzyme. The column was washed with the same buffer solution, then the same buffer solution but containing 0.025M NaCl, followed by elution with the same buffer solution containing 0.1M NaCl to obtain fractions exhibiting the enzyme activity (step 3).

After the addition of about 5 times by volume of water, the fractions with the enzyme activity was absorbed in S-Sepharose column which was equilibrated with 5 mM phosphate buffer solution (pH 6.5 to 7.0) in advance. The column was washed with the same buffer solution, then the same buffer solution but containing 0.025M NaCl, followed by gradient elution with the same buffer solution containing linear concentration gradient of 0.025 to 0.35M NaCl to obtain fractions exhibiting enzyme activity.

The eluted chondroitinase ABC solution exhibited a single band (SDS-PAGE), with nucleic acid (DNA), , protease, etc. having been removed, and had a specific activity of 380 U/mg, which was about three times higher than the specific activity of chondroitinase ABC obtained by a conventional method. Thus the chondroitinase ABC was a high-purity enzyme.

To the enzyme solution (a phosphate buffer solution, pH 7.0) was added polyethylene glycol (molecular weight: 4,000) so as to give a concentration of 15%, and the mixture was allowed to stand at room temperature for about one week to produce white or colorless needle-like or prismatic crystals of chondroitinase ABC. A microscope photography (magnification: 2.5) of the crystals is given in FIG. 1.

The crystals were rhombic or monoclinic system needle-like crystals, having the following crystal parameters identified by X-ray crystal structure analysis.

|  | Rhombic system | Monoclinic system |
|---|---|---|
| Space group | $P222_1$ | $P2_1$ |
| Lattice constant | $a = 214$ Å | $a = 214$ Å |
|  | $b = 92$ Å | $b = 56$ Å |
|  | $c = 56$ Å | $c = 92$ Å |
|  | $\alpha = 90°$ | $\alpha = 90°$ |
|  | $\beta = 90°$ | $\beta \geq 90°$ |
|  | $\gamma = 90°$ | $\gamma = 90°$ |

Figure 7:
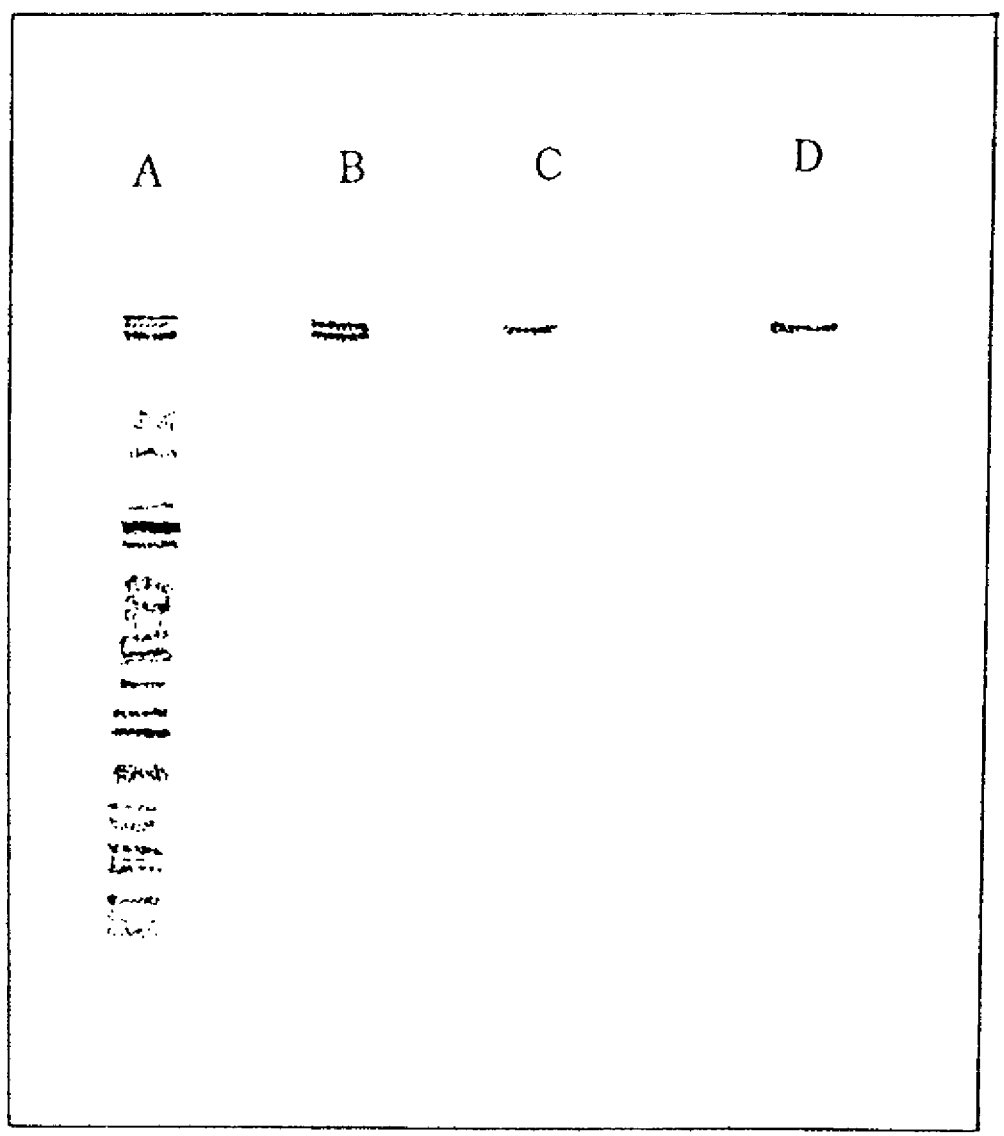
FIG. 7 shows SDS-PAGE bands in different steps of the process for the purification of the chondroitinase ABC in Example 1, wherein band A is a band exhibited by the protamine treatment supernatant; band B, the CM-Sepharose treatment liquid; band C, the S-Sepharose treatment liquid (unreduced); and band D, the S-Sepharose treatment liquid (reduced).

The results of SDS-PAGE in each purification step are shown in FIG. 7.

SDS-PAGE was carried out according to a common method (Laemmli, U.K., Nature, 227, 680–685 (1970)) using 10% gel.

A clear single band was seen in both unreduced and reduced states when the enzyme was treated with S-Sepharose™ (see FIGS. 7; C and D).

The degrees of purification of chondroitinase ABC in each purification step in the process of the present invention is shown in Table 3.

TABLE 3

| Step | Total activity (U) | Total protein (mg) | Specific activity (U/mg) | Purity (times) | Yield (%) |
|---|---|---|---|---|---|
| Extract (Step 1) | 75000 | 37000 | 2 | 1 | 100 |
| Protamine treated solution (Step 2) | 58000 | 1600 | 36 | 18 | 77 |
| CM-Sepharose treated solution (Step 3) | 43000 | 240 | 180 | 90 | 57 |
| S-Sepharose treated solution (Step 4) | 31000 | 82 | 380 | 190 | 41 |

Contents of endotoxin and residual amounts of protease are shown in Table 4.

TABLE 4

| | Endotoxin content* | | Total protease** | |
|---|---|---|---|---|
| Step | pg/100 U | EU/100 U | µg | % |
| Extract (Step 1) |  |  | 320 | 100 |
| Protamine treated solution (Step 2) | $8.1 \times 10^8$ | $2.3 \times 10^6$ | 64 | 20 |
| CM-Sepharose treated solution (Step 3) | $6.7 \times 10^5$ | $1.9 \times 10^3$ | 30 | 9 |
| S-Sepharose treated solution (Step 4) | 5.0 | $1.4 \times 10^{-2}$ | <0.3 | <0.1 |

*The endotoxin content for 100 unit (U) of chondroitinase ABC; Measured by Toxicolor system (trademark, a product of Seikagaku Corporation). EU designates an endotoxin unit.
**Measured using FITC-casein as a substrate No substantial amount of endotoxin was contained in the enzyme solution obtained in step 4. Its content was only trace; 5.0 pg/100 U as shown in the above Table. Also, as a result of the measurement of nucleic acid (DNA) by the threshold method (DNA measurement device, Threshold, trademark, manufactured by Molecular Device Co.), no DNA was detected, proving that the DNA content is below the detectable limit.

Table 5 shows the stability of the chondroitinase ABC obtained in step 4 of the present invention, when the enzyme was left in a solution at different temperatures. In the Table, the stability is indicated by the relative activity to −40° C. (as 100%), when a 350 U/ml solution was stored for 5 days.

TABLE 5

| Temperature °C. | Relative activity (%) |
|---|---|
| −40 | 100 |
| 4 | 109 |
| Room temperature | 109 |
| 37 | 91 |

Example 2

7.5 kg of wet cells of Proteus vulgaris (NCTC 4636, ATCC 6896, IFO 3988) used in Example 1 was charged into a tank containing about 15 L of 40 mM phosphate buffer solution (pH 7.0±0.5) to which 10% polyoxyethylene lauryl ether (POELE; Nikkol BL-9EX) was added and about 7.5 L of purified water. The mixture was stirred to obtain a cell suspension, which was warmed at 35° C.±3° C. and stirred for about two hours at this temperature. After about two hours, about 30 L of 20 mM phosphate buffer solution (pH 7.0±0.5) was added to dilute the suspension. The suspension was then cooled to 20° C.

The suspension was centrifuged by a sharpless centrifuge to obtain a supernatant. The temperature of the solution was kept below 20° C. before and after the centrifuge.

The supernatant thus obtained was diluted with the addition of about 30 L of purified water which was cooled to 2° to 150° C., and passed through CM-Sepharose column (gel amount: about 5 L) to absorb the chondroitinase ABC to the column.

The column was washed with 1 L of purified water, 10 L of 0.5% POELE aqueous solution, and 5 L of 0.04M phosphate buffer solution (pH 6.2±0.2). Next, the column was linear gradiently eluted with about 20 L of 0.04M phosphate buffer solution (pH 6.2±0.2) containing concentration gradient of 0 to 0.25M NaCl to obtain fractions exhibiting chondroitinase ABC activity.

The eluate was passed through a sterilizing filter with a pore size of 0.22 μm and collected in a sterilized container, thus obtaining a chondroitinase ABC solution.

The relationship between the cell extraction time (hour) and the enzyme activity is shown in Table 6.

TABLE 6

| Steps | Time elapsed (hr) | Total enzyme activity (× 10⁴ u) | Amount of solution (l) |
|---|---|---|---|
| Immediately after suspension | 0 | 54.3 | 35 |
| At commencement of stirring (32° C.) | 0 | 301 | 35 |
| After stirring | 0.25 | 460 | 35 |
|  | 0.5 | 491 | 35 |
|  | 1.0 | 538 | 35 |
|  | 1.5 | 509 | 35 |
|  | 2.0 | 515 | 35 |
| Supernatant by centrifugation |  | 383 | 60 |

The enzyme concentration was equilibrated within 1 to 2 hours after commencement of the cell extraction.

The total nucleic acid in the extract reached a maximum (about 25 g) at 0.25 hour after commencement of the stirring, decreased thereafter, and was equilibrated (about 2 to 3 g) after about one hour.

Example 3

5 kg of wet cells of Proteus vulgaris (NCTC 4636, ATCC 6896, IFO 3988) used in Example 1 was charged into a 5-fold volume of 20 mM phosphate buffer solution (pH 7.0) to which 5% POELE was added, and extracted for 3 hours at 37° C. The extract was subjected to the protamine treatment, CM-Sepharose chromatography, and S-Sepharose chromatography in the same manner as in Example 1 (the conditions of the separation are shown in Table 7), and gradiently eluted to obtain a chondroitinase ABC:. The solution exhibited a single band of chondroitinase ABC in SDS-PAGE. The solution was passed through a sterilizing filter with a pore size of 0.22 μm by a feed pump and collected in a sterilized container, thus obtaining a chondroitinase ABC solution.

Calculation of the data given in Table 7 indicates the extraction of the chondroitinase ABC of about 500 units per one g of the cells.

The degree of the purification in each step in Example 3 is shown in Table 7.

TABLE 7

| Steps | Total enzyme activity (× 10⁴ u) | Recovery yield (%) | Endotoxin (pg/100 u) |
|---|---|---|---|
| Frozen cells | 295 | — | — |
| Extract | 262 | 88.8* | — |
| Protamine treatment | 203 | 68.8* | — |
| CM-Sepharose treatment |  |  |  |
| Effluent | 4 | 2.0 | — |
| Washing I (Phosphate buffer containing 0.5% POELE) | 0.1 | <0.1 | — |
| Washing II (25 mM NaCl) | 3.3 | 1.6 | — |
| Eluate (100 mM NaCl) | 157 | 77.4 | 1,300 |
| Sterilized filtrate | 158 | 77.8 | 341 |
| S-Sepharose treatment |  |  |  |
| Effluent | 0 | 0 | — |
| Washing I (Distilled water) | 0.1 | <0.1 | — |
| Washing II (50 mM NaCl) | 0.5 | 2.5 | — |
| Eluate | 150 | 73.9 | 3.4 |

*indicates a recovery rate from frozen cell; other recovery rate data were obtained from protamine treated solution.

Figure 8:
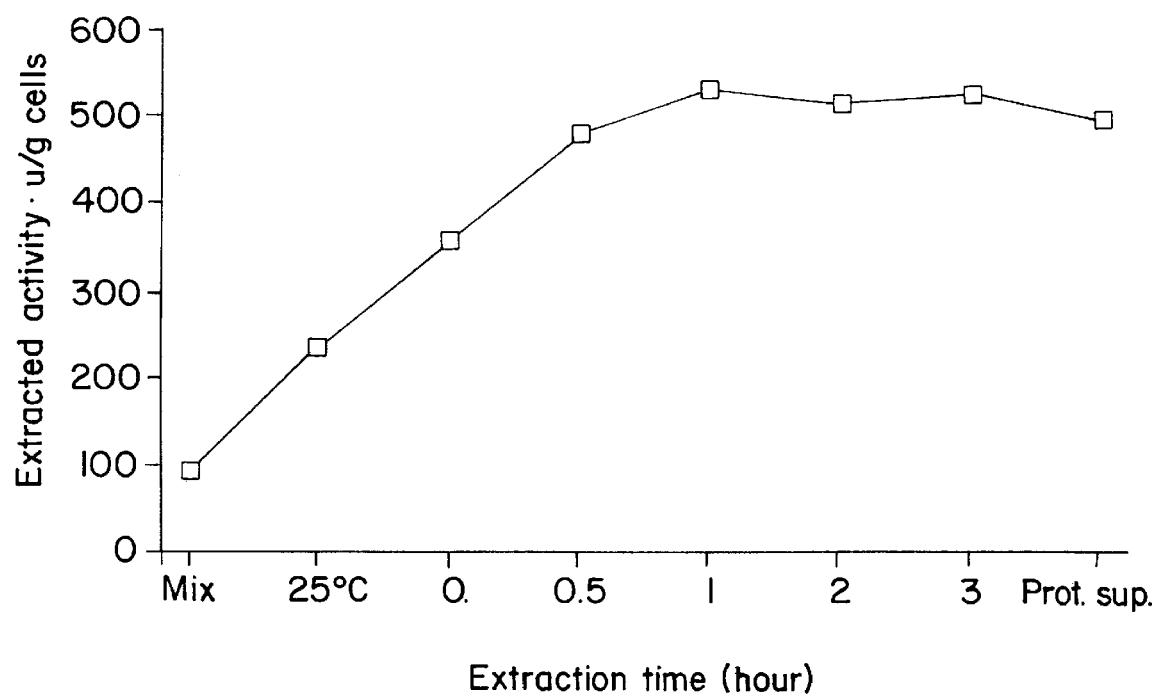
FIG. 8 shows a relationship between the extraction time of the chondroitinase ABC from bacterial cells and the activity of the chondroitinase ABC in Example 3.
Figure 9:
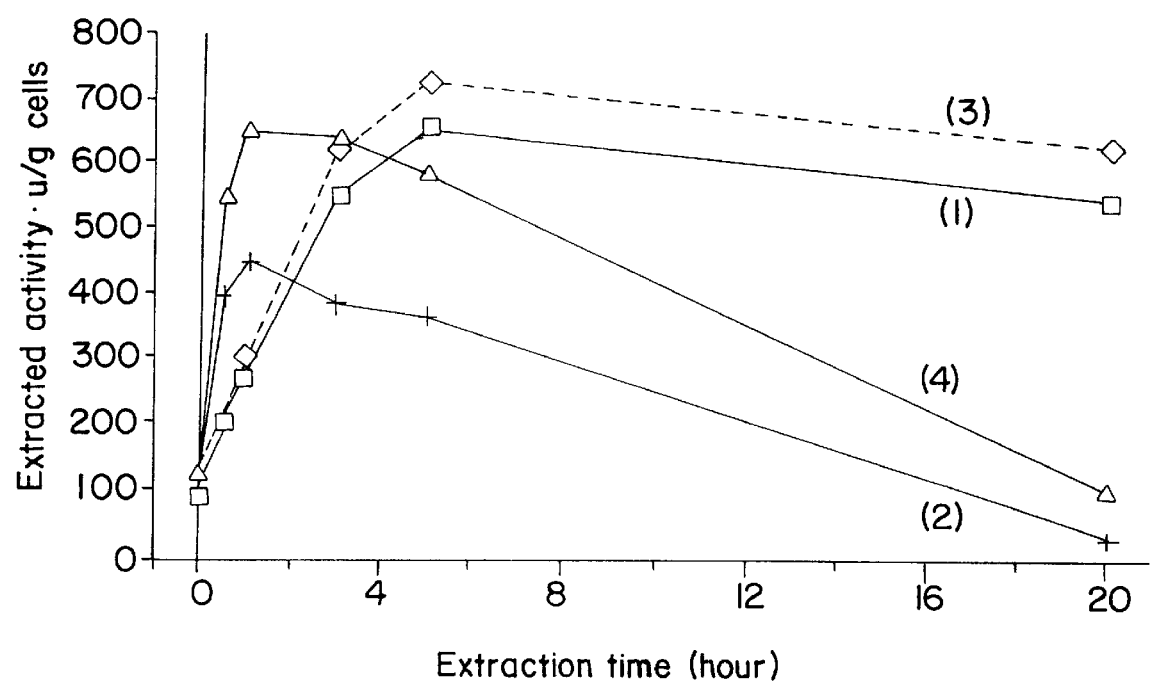
FIG. 9 shows a relationship between the time required for the extraction of bacterial cells using Triton X-100-containing buffer solutions with different concentrations and the activity of the chondroitinase ABC in Example 4, wherein curve 1 indicates the extraction using a buffer solution with a surfactant concentration of 2% at 25° C.; curve 2, a buffer solution with a surfactant concentration of 2% at 37° C.; curve 3, a buffer solution with a surfactant concentration of 5% at 25° C.; and curve 4, a buffer solution with a surfactant concentration of 5% at 37° C.
Figure 10:
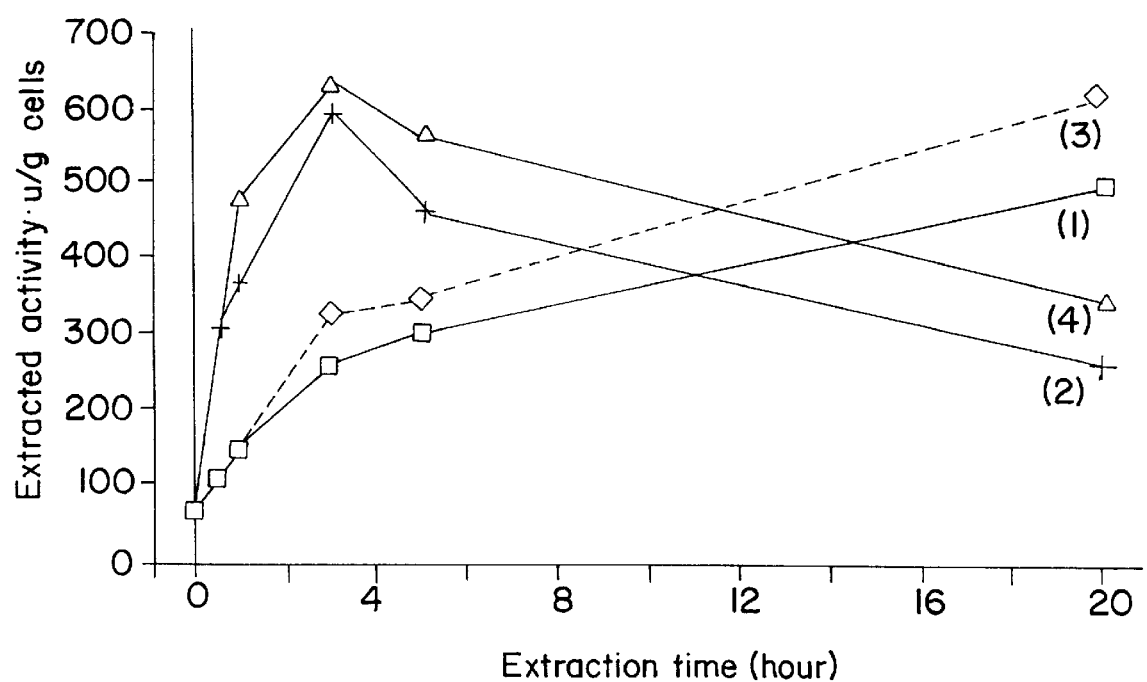
FIG. 10 shows relationships between the time required for the extraction of bacterial cells using Brij-35-containing buffer solutions with different concentrations and the activity of the chondroitinase ABC in Example 4, wherein curve 1 indicates the extraction using a buffer solution with a surfactant concentration of 2% at 25° C.; curve 2, a buffer solution with a surfactant concentration of 2% at 37° C.; curve 3, a buffer solution with a surfactant concentration of 5% at 25° C.; and curve 4, a buffer solution with a surfactant concentration of 5% at 37° C.
Figure 11:
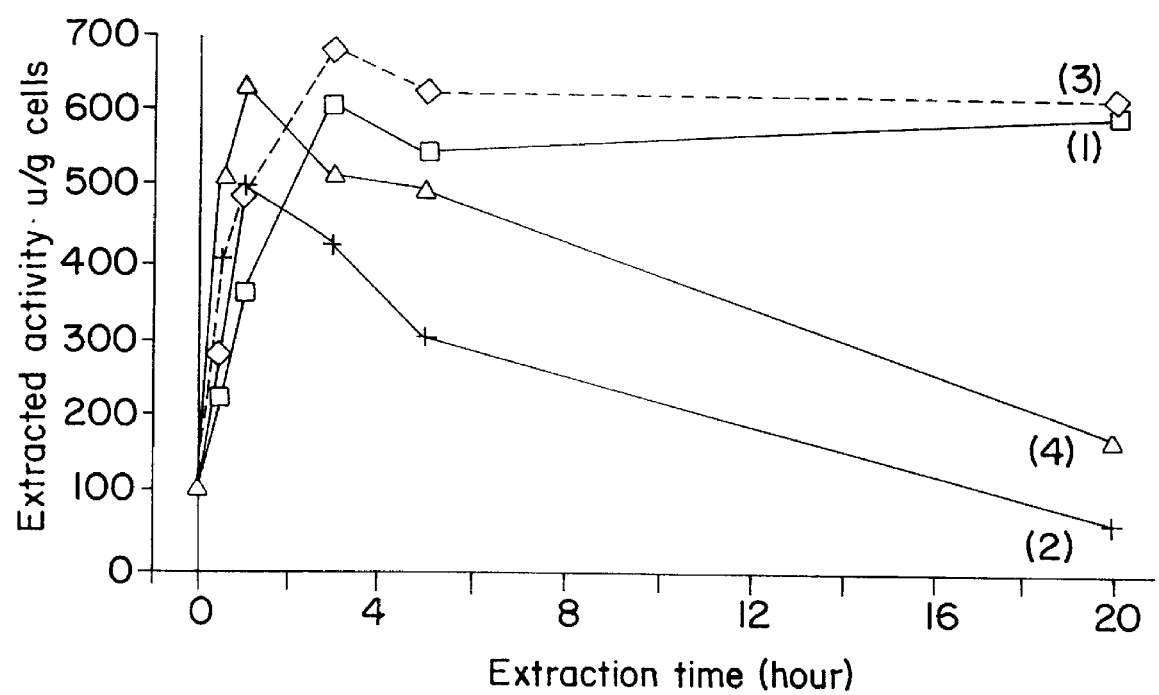
FIG. 11 shows relationships between the time required for the extraction of bacterial cells using Nonidet P-40-containing buffer solutions with different concentrations and the activity of the chondroitinase ABC in Example 4, wherein curve 1 indicates the extraction using a buffer solution with a surfactant concentration of 2% at 25° C.; curve 2, a buffer solution with a surfactant concentration of 2% at 37° C.; curve 3, a buffer solution with a surfactant concentration of 5% at 25° C.; and curve 4, a buffer solution with a surfactant concentration of 5% at 37° C.
Figure 12:
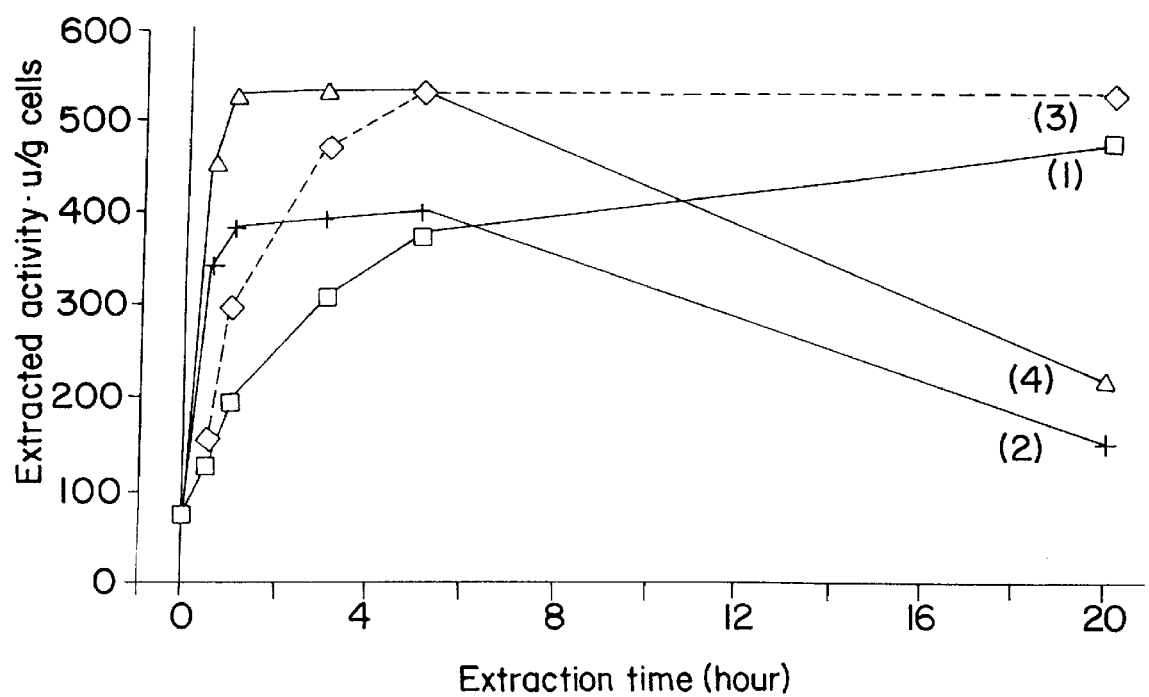
FIG. 12 shows relationships between the time required for the extraction of bacterial cells using POELE-containing buffer solutions with different concentrations and the activity of the chondroitinase ABC in Example 4, wherein curve 1 indicates the extraction using a buffer solution with a surfactant concentration of 2% at 25° C.; curve 2, a buffer solution with a surfactant concentration of 2% at 37° C.; curve 3, a buffer solution with a surfactant concentration of 5% at 25° C.; and curve 4, a buffer solution with a surfactant concentration of 5% at 37° C.

The relationship between the time required for the chondroitinase ABC to be extracted from the cells and the activity of the chondroitinase ABC is shown in FIG. 8.

Example 4

Triton X-100, Brij-35, Nonidet P 40 was added so as to give a concentration of 2% and 5% to prepare suspensions in the same manner as in Example 3 using POELE. Extraction of chondroitinase ABC was performed at 25° C. or 37° C. The results are shown in FIGS. 9–12, which shows that the cases where extraction was carried out at 37° C. and using surfactants at a concentration of 5% produced extracts exhibiting higher activity and purified equilibrated within 2 to 4 hours.

Example 5

<Effect of Preventing Adhesion to Glass and Plastic Containers (Solutions)>

Solutions of chondroitinase ABC composition were obtained from 5 units (U) of the chondroitinase ABC prepared in Example 1 (specific activity: 300 u/mg) and purified gelatin (acid treated gelatin), human serum albumin (HSA), or bovine serum albumin (BSA), each in amounts of 0.001 to 100 times of the enzyme protein, as shown in Tables 8 and 9. The pH was adjusted to 7.0 with the addition of 50 mM potassium phosphate buffer solution. These solutions were charged into vials made of glass or plastic (polypropylene) and stored for 24 hours at 4° C., following which the enzyme activities in solutions were measured to investigate their effects of preventing adhesion to the containers. The results are expressed by percentage of the activity in the solutions after storing for that of before storing, and are given in Table 8 (glass vials) and Table 9 (plastic vials).

TABLE 8

Adhesion to glass containers

| Additive | Amount of additives (times) | | | | | | |
|---|---|---|---|---|---|---|---|
| | 0 | 0.001 | 0.01 | 0.1 | 1 | 10 | 100 |
| Gelatin | 65 | 78 | 87 | 98 | 99 | 103 | 96 |
| HSA | 65 | 82 | 92 | 100 | 102 | 98 | 101 |
| BSA | 65 | 80 | 94 | 98 | 96 | 99 | 100 |

TABLE 9

Adhesion to plastic containers

| Additive | Amount of additives (times) | | | | | | |
|---|---|---|---|---|---|---|---|
| | 0 | 0.001 | 0.01 | 0.1 | 1 | 10 | 100 |
| Gelatin | 75 | 84 | 98 | 101 | 98 | 100 | 104 |
| HSA | 75 | 86 | 98 | 99 | 100 | 105 | 99 |
| BSA | 75 | 85 | 96 | 103 | 101 | 105 | 102 |

Example 6
<Effect of Preventing Formation of Insoluble Matters and Effect of Maintaining the Activity when Reconstitution (lyophilized composition)>

Solutions of chondroitinase ABC composition were obtained from 50 units (U) of chondroitinase ABC (specific activity: 380 U/mg) and materials shown in Tables 10 and 11, each in amounts of 0.001 to 10 times of the enzyme protein, as shown in Tables 10 and 11. The pH was adjusted to 6.5 with the addition of 20 mM sodium phosphate buffer solution. After the addition of creatinine (10 mg/ml) as an excipient, these solutions were charged into vials and freeze-dried to obtain a dry chondroitinase ABC composition. The compositions were stored for one month at 40° C. in the vials to observe their properties to find no abnormality such as discoloration, deformation, and the like. Water for injection was added to observe their properties when reconstituted and their activities were measured to examine the activity maintenance effect of the additive. The results are shown in Tables 10 and 11. Table 10 shows the results of the naked eye observation as to the presence or absence of insoluble matters when the composition was reconstituted, and Table 11 shows the activity after storage in percentage of the activity before the storage.

In the same manner as above a composition (chondroitinase ABC: 50 U, specific activity: 380 U/mg; HSA: 0.05 time of the enzyme protein) to which no creatinine was added was prepared to observe the property and to measure the activity after storage to find that the solution was colorless and clear, and maintained 80% residual activity.

TABLE 10

Property after reconstitution

| Additive | Amount of additives (times) | | | | | | |
|---|---|---|---|---|---|---|---|
| | 0 | 0.001 | 0.01 | 0.05 | 0.1 | 1 | 10 |
| Gelatin | + | − | − | − | − | − | − |
| HSA | + | − | − | − | − | − | − |
| BSA | + | − | − | − | − | − | − |

−: colorless and clear
+: insoluble matters were observed

TABLE 11

Residual Activity after storage

| Additive | Amount of additives (times) | | | | | | |
|---|---|---|---|---|---|---|---|
| | 0 | 0.001 | 0.01 | 0.05 | 0.1 | 1 | 10 |
| Gelatin | 0.3 | 24 | 47 | 80 | 96 | 100 | 98 |
| HSA | 0.3 | 23 | 45 | 83 | 99 | 98 | 98 |
| BSA | 0.3 | 20 | 50 | 77 | 92 | 100 | 94 |

The above experimental results demonstrate that the addition of gelatin, HSA, or BSA to purified chondroitinase and the adjustment of pH to the neighborhood of neutral in a solution prevents adhesion of purified chondroitinase to containers, makes the solution colorless and transparent after dissolution, and maintains the enzyme without lowering its activity during storage.

These effects are especially remarkable when gelatin, HSA, or BSA is used in an amount of 0.05 to 10 times of the enzyme protein of the purified chondroitinase. In this instance, a particularly preferred chondroitinase composition is a chondroitinase ABC composition prepared by using a high-purity chondroitinase ABC having a high specific activity together with gelatin, HSA, or BSA, and dissolving them in a sodium phosphate buffer solution with pH 5 to 9, preferable 6 to 8, to make a solution (10 to 50 nM as a sodium phosphate buffer concentration), and lyophilizing it. It is desirable that the lyophilized composition provides a solution having the pH of the above range when it was dissolved.

Example 7

<Effect of Preventing Adhesion to Glass Containers>

Chondroitinase ABC (0.4 unit or 4 unit) was dissolved into 0.1M aqueous solution of NaCl. To the solution was added Polysorbate 80 in amounts of 0.075 to 75 times of the amount of enzyme protein (1.33 μg or 13.3 μg), followed by the addition of a phosphate buffer solution to adjust pH to 6.9. This solution was filled in ampules made of glass to obtain a pharmaceutical composition. The ampules were stored at 20° C. for 20 hours to measure its titer and examine the effect of preventing adhesion to containers. The results are shown in Table 12.

TABLE 12

| Chondroitinase ABC | residual relative activity (%) | | | | |
|---|---|---|---|---|---|
| | Amount of Polysorbate 80 (times) | | | | |
| (Unit) | 0 | 0.075 | 0.75 | 7.5 | 75 |
| 0.4 | 68 | | 78 | 84 | 93 |
| 4 | 71 | 89 | 84 | 110 | |

Example 8
<Effect of Preventing Production of Insoluble Matters by Shaking>

Chondroitinase ABC (40 units) was dissolved into 0.1M aqueous solution of NaCl. To the solution was added Polysorbate 80 in amounts of 0.0075 to 7.5 times of the amount of enzyme protein (133 μg), as shown in Table 13, followed by the addition of a phosphate buffer to adjust pH to 6.9. This buffer was filled in ampules made of glass. The ampules were shaken using a shaking incubator at 160 times per minute for 8 hours to observe the presence or absence of insoluble matters produced. The results are shown in Table 13.

TABLE 13

| | Amount of Polysorbate (times) | | | | |
|---|---|---|---|---|---|
| Additive | 0 | 0.0075 | 0.075 | 0.75 | 7.5 |
| Polysorbate 80 | Present | Present | Absent | Absent | Absent |
| Polysorbate 60 | Present | — | — | — | Absent |
| Polysorbate 40 | Present | — | — | — | Absent |

Example 9
<Effect of Preventing Formation of Insoluble Matters by Vibration During Transportation>

Chondroitinase ABC (5 unit) was dissolved into 0.1M aqueous solution of NaCl. To the solution was added Polysorbate 80 in amounts of 0.060 to 6.0 times of the amount of enzyme protein (16.7 μg), followed by the addition of a phosphate buffer solution to adjust pH to 6.9. This solution was filled in ampules made of glass. The ampules were transported in a truck at a temperature of below 25° C. for 7 days to observe the presence or absence of insoluble matters formed. The results are shown in Table 14.

TABLE 14

<Chondroitinase ABC: 5 Units>

| Amount (times) of | Transported distance (km) | |
|---|---|---|
| Polysorbate 80 | 800 | 1200 |
| 0 | Present | Present |
| 0.060 | Present | Present |
| 0.60 | Absent | Present |
| 6.0 | Absent | Absent |

Example 10
<Effect of Preventing Formation of Insoluble Matters by Vibration During Transportation>

Chondroitinase ABC (50 units) was dissolved into 0.1M aqueous solution of NaCl. To the solution was added Polysorbate 80 in amounts of 0.0060 to 0.60 times of the amount of enzyme protein (167 μg), followed by the addition of a phosphate buffer solution to adjust pH to 6.9. This solution was filled in ampules made of glass. The ampules were transported in a truck at a temperature of below 25° C. for 7 days to observe the presence or absence of insoluble matters formed. The results are shown in Table 15.

TABLE 15

<Chondroitinase ABC: 50 Units>

| Amount (times) of | Transported distance (km) | |
|---|---|---|
| Polysorbate 80 | 800 | 1200 |
| 0 | Present | Present |
| 0.0060 | Present | Present |
| 0.060 | Absent | Present |
| 0.60 | Absent | Absent |

Example 11
<Effect of Preventing Formation of Insoluble Matters by Vibration During Transportation>

Chondroitinase ABC (140 units) was dissolved into 0.1M aqueous solution of NaCl. To the solution was added Polysorbate 80 in an amount of 32 times of the amount of enzyme protein (467 μg), followed by the addition of a phosphate buffer solution to adjust pH to 6.9. This solution was filled in ampules made of glass. The ampules were transported in a truck at a temperature of below 22.6° C. for 16 days to observe the presence or absence of insoluble matters formed. Further, the titer was measured to calculate the residual rate. The results are shown in Tables 16 and 17.

TABLE 16

<Chondroitinase ABC: 140 Units>

| Amount (times) of | Transported distance (kin) | | | |
|---|---|---|---|---|
| Polysorbate 80 | 800 | 1200 | 1600 | 2000 |
| 32 | Absent | Absent | Absent | Absent |

TABLE 17

<Chondroitinase ABC: 140 Units>

| Amount (times) of Polysorbate 80 | Residual rate after transportation |
|---|---|
| 32 | 88–93% |

Example 12
<Effect of Preventing Formation of Insoluble Matters by Vibration During Transportation>

Chondroitinase ABC (5 units) was dissolved into 0.1M aqueous solution of NaCl. To the solution was added Polysorbate 80 in an amount of 30 to 300 times of the amount of enzyme protein (16.7 μg), followed by the addition of a phosphate buffer solution to adjust pH to 6.9. This solution was filled in ampules made of glass. The ampules were transported in a truck at a temperature of below 11.7° C. for 19 days to observe the presence or absence of insoluble matters formed. Further, the titer was measured to calculate the residual rate. The results are shown in Tables 18 and 19.

TABLE 18

| <Chondroitinase ABC: 5 Units> | | | | |
|---|---|---|---|---|
| Amount (times) of | Transported distance (km) | | | |
| Polysorbate 80 | 800 | 1200 | 1600 | 2000 |
| 30 | Absent | Absent | Present | Present |
| 90 | Absent | Absent | Absent | Absent |
| 300 | Absent | Absent | Absent | Absent |

TABLE 19

| <Chondroitinase ABC: 5 Units | |
|---|---|
| Amount (times) of Polysorbate 80 | Residual rate after transportation |
| 30 | 95–101% |
| 90 | 102–107% |
| 300 | 110–114% |

Example 13

<Effect of Preventing Formation of Insoluble Matters by During Transportation>

Chondroitinase ABC (50 units) was dissolved into 0.1M aqueous solution of NaCl. To the solution was added Polysorbate 80 in an amount of 3.0 to 30 times of the amount of enzyme protein (167 µg), followed by the addition of a phosphate buffer solution to adjust pH to 6.9. This solution was filled in ampules made of glass. The ampules were transported in a truck at a temperature of below 11.7° C. for 19 days to observe the presence or absence of insoluble matters produced. Further, the titer was measured to calculate the residual rate. The results are shown in Tables 20 and 21.

TABLE 20

| <Chondroitinase ABC: 50 Units > | | | | |
|---|---|---|---|---|
| Amount (times) of | Transported distance (km) | | | |
| Polysorbate 80 | 800 | 1200 | 1600 | 2000 |
| 3.0 | Absent | Absent | Present | Present |
| 9.0 | Absent | Absent | Absent | Absent |
| 30 | Absent | Absent | Absent | Absent |

TABLE 21

| <Chondroitinase ABC: 50 Units> | |
|---|---|
| Amount (times) of Polysorbate 80 | Residual rate after transportation |
| 3.0 | 100–101% |
| 9.0 | 102–103% |
| 30 | 100–103% |

Example 14

Chondroitinase ABC (30 units) was dissolved into 0.1M aqueous solution of NaCl. To the solution was added Pluronic F68 in an amount of 15 times of the amount of the enzyme (100 µg), followed by the addition of a phosphate buffer solution to adjust pH to 7. This solution was filled in ampules made of glass to obtain a pharmaceutical composition.

Chondroitinase ABC (80 units) was dissolved into 0.1M aqueous solution of NaCl. To the solution was added HCO-60 in an amount of 15 times of the amount of the enzyme (267 µg), followed by the addition of a phosphate buffer solution to adjust pH to 7. This solution was filled in ampules made of glass to obtain a pharmaceutical composition.

Chondroitinase ABC (30 units) was dissolved into 0.1M aqueous solution of NaCl. To the solution was added Polysorbate 80 in an amount of 15 times of the amount of the enzyme (100 µg), followed by the addition of a phosphate buffer solution to adjust pH to 7. This solution was filled in ampules made of glass to obtain a pharmaceutical composition.

Chondroitinase ABC (60 units) was dissolved into 0.1M aqueous solution of NaCl. To the solution was added Polysorbate 80 and Pluronic F68, each in an amount of 7.5 times of the amount of the enzyme (200 µg), followed by the addition of a phosphate buffer solution to adjust pH to 7. This solution was filled in ampules made of glass to obtain a pharmaceutical composition.

Chondroitinase ABC (50 units) was dissolved into 0.1M aqueous solution of NaCl. To the solution was added HCO-60 and DK ester F-160, each in an amount of 7.5 times of the amount of the enzyme (167 µg), followed by the addition of a phosphate buffer solution to adjust pH to 7. This solution was filled in ampules made of glass to obtain a pharmaceutical composition.

Obviously, numerous modifications and variations of the present invention are possible in light of the above teachings. It is therefore to be understood that within the scope of the appended claims, the invention may be practiced other than as specifically described herein.

What is claimed is:

1. Purified crystalline chondroitinase ABC isolated from *Proteus vulgaris* ATCC 6896 comprising the following characteristics:

(i) a molecular weight of about 100,000 daltons represented by a single band as measured by SDS-polyacrylamide gel electrophoresis (SDS-PAGE), in a reduced or unreduced state, and a single peak as measured by gel permeation chromatography, (ii) isoelectric points of about 8.2 and about 8.5, (iii) an optimum pH of from about 8.0 to 8.2, (iv) an optimum reaction temperature of 37° C., and (v) a specific activity of 300 U/mg or more;

wherein activity of the chondroitinase ABC is inhibited by contact with at metal ion selected from the group consisting of $Zn^{2-}$, $Ni^{2-}$, $Fe^{3-}$, and $Cu^{2-}$.

2. The purified crystalline chondroitinase ABC of claim 1 wherein said crystals are needle-like or prismatic crystals.

3. The purified crystalline chondroitinase ABC of claim 2 prepared by crystallization in a polyether having hydroxy groups at both ends.

4. The purified crystalline chondroitinase ABC of claim 1 having alanine as an N-terminal amino acid residue and proline as a C-terminal amino acid residue.

5. Needle-like or prismatic crystals of chondroitinase ABC isolated from *Proteus vulgaris* ATCC 6896 comprising crystals having rhombic or monoclinic system and further comprising the following crystal parameters:

|  | Rhombic system | Monoclinic system |
| --- | --- | --- |
| Space group | $P222_1$ | $P2_1$ |
| Lattice constant | a = 214 Å | 2 = 214 Å |
|  | b = 92 Å | b = 56 Å |
|  | c = 56 Å | c = 92 Å |
|  | α = 90° | α = 90° |
|  | β = 90° | β ≧ 90° |
|  | γ = 90° | γ = 90°. |

* * * * *

SEQUENCE LISTING ( 1 ) GENERAL INFORMATION:

( i i i ) NUMBER OF SEQUENCES: 2

( 2 ) INFORMATION FOR SEQ ID NO:1:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..9
        (D) OTHER INFORMATION: /note= "N-terminal sequence of
              Chondroitinase ABC"

(xi) SEQUENCE DESCRIPTION: SEQ ID NO:1:

Ala  Thr  Xaa  Asn  Pro  Ala  Phe  Asp  Pro
    1                    5

(2) INFORMATION FOR SEQ ID NO:2:

(i) SEQUENCE CHARACTERISTICS:
        (A) LENGTH: 3 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..3
        (D) OTHER INFORMATION: /note= "C-terminal sequence of
              Chondroitinase ABC"

(xi) SEQUENCE DESCRIPTION: SEQ ID NO:2:

Ser  Leu  Pro
    1